United States Patent [19]
Webb, II

[11] Patent Number: 5,976,176
[45] Date of Patent: Nov. 2, 1999

[54] BODY HEATING DEVICE

[76] Inventor: Matt M Webb, II, 8174 N. Dixie Hwy., Newport, Mich. 48166

[21] Appl. No.: 08/963,610

[22] Filed: Oct. 31, 1997

[51] Int. Cl.$^6$ ..................................................... A61F 7/00
[52] U.S. Cl. ........................... 607/104; 607/112; 607/114
[58] Field of Search ..................... 607/96, 104, 107–112, 607/114; 165/46; 126/204; 128/207.12

[56] References Cited

U.S. PATENT DOCUMENTS

| | | | |
|---|---|---|---|
| D. 280,775 | 10/1985 | Bisbee | D2/29 |
| 3,153,720 | 10/1964 | Petronio et al. | 607/108 X |
| 3,229,681 | 1/1966 | Gluckstein | 607/108 X |
| 4,067,064 | 1/1978 | Cerniway et al. | 2/2.1 |
| 4,286,439 | 9/1981 | Pasternack | 62/259.3 |
| 4,503,850 | 3/1985 | Pasternak | 307/108 X |
| 4,572,188 | 2/1986 | Augustine et al. | 128/380 |
| 4,691,762 | 9/1987 | Elkins et al. | 165/46 X |
| 5,383,918 | 1/1995 | Panetta | 607/104 |
| 5,386,701 | 2/1995 | Cao | 62/259.3 |

*Primary Examiner*—Cary O'Connor
*Assistant Examiner*—Ryan Carter
*Attorney, Agent, or Firm*—Goldstein & Canino

[57] ABSTRACT

A body heating device which utilizes heat from one's own breath to warm various designated body parts during a cold outdoor activity. The device comprises a central conduit having a mouth opening, said central conduit connected to a network of tubes, and an attachment means for attaching said tubes and conduit to a person's body. The body heating device preferably includes a distribution control assembly connected between said central conduit and said network of tubes, for allowing the person to select the amount of heated air to be delivered to different body parts. The body heating device is worn on the person's body, and each of the open ends of the tubes are placed near those areas of the body to which hot air is to be delivered. By blowing air into the mouth opening end of said central conduit, a pocket of hot air travels to the open ends of the tubes, thereby delivering hot air to the selected body parts.

3 Claims, 2 Drawing Sheets

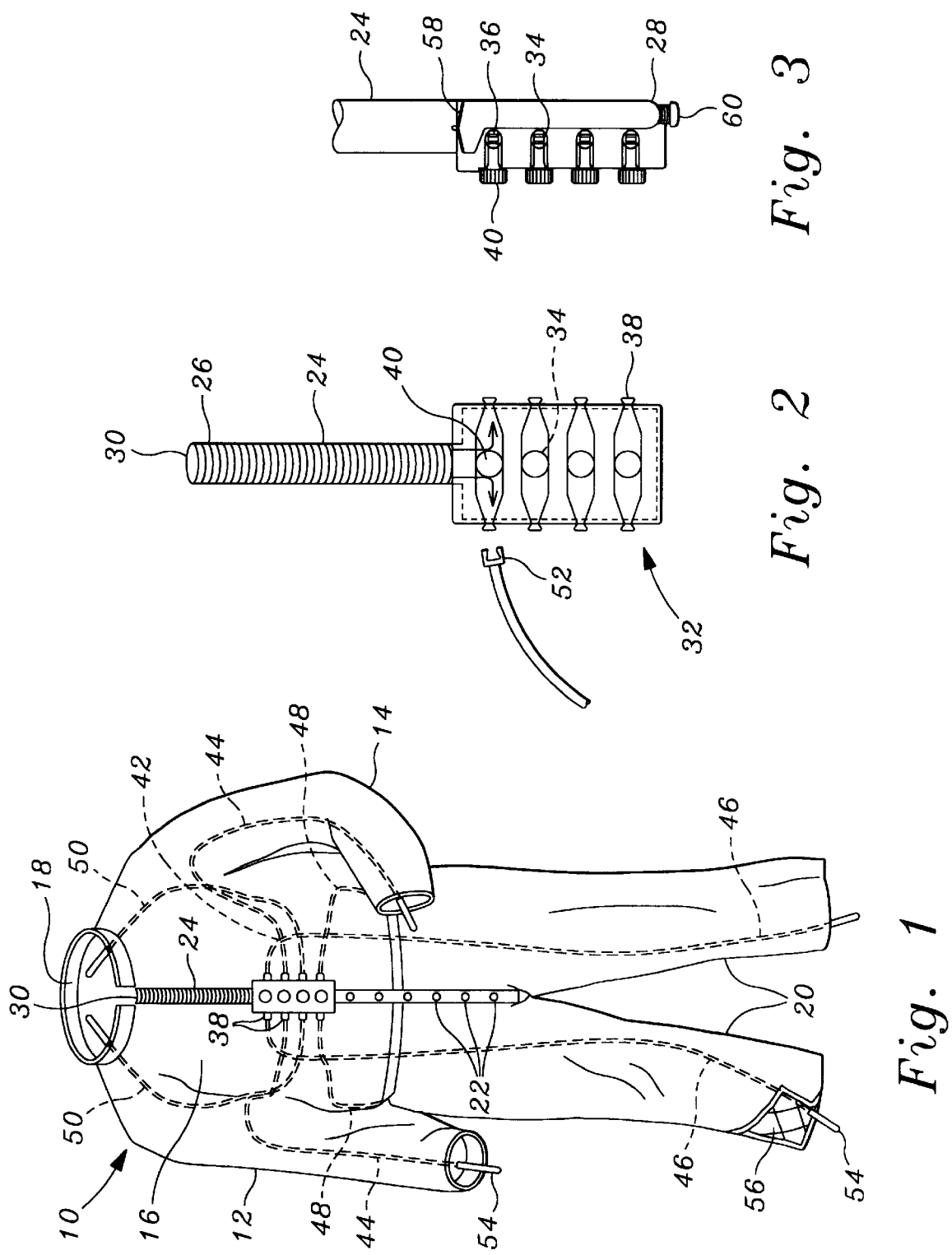

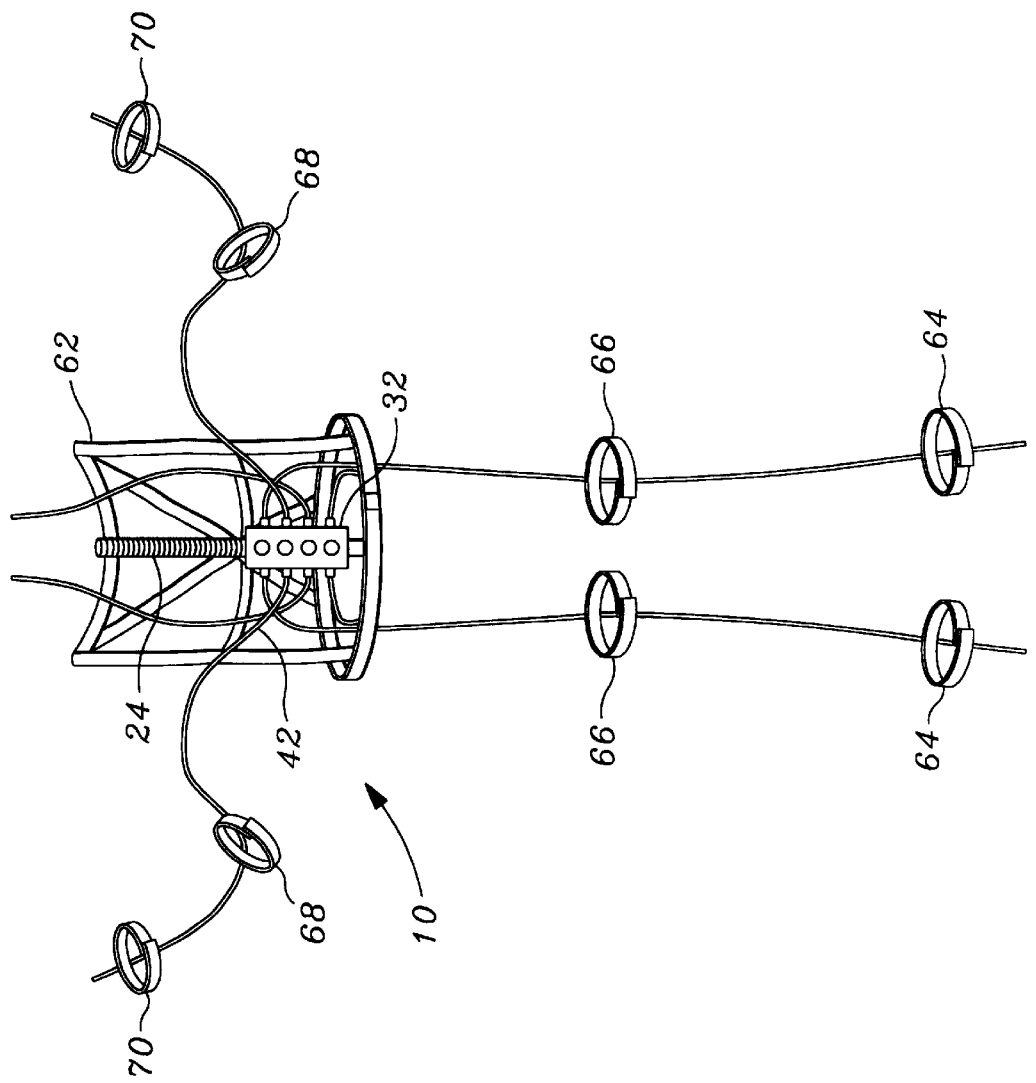

BODY HEATING DEVICE

BACKGROUND OF THE INVENTION

This invention relates to a body heating device. More particularly, the invention relates to a body heating device which utilizes heat from one's own breath to keep selected body parts warm.

Hunting, fishing, and many other outdoor activities often require a person to stand still in one position for a very long period of time. Particularly in cold weather, such lack of movement hinders circulation of blood to one's extremities, overall neck and kidney areas, and eventually causes one's overall body temperature to drop to a potentially dangerous level. The reduction of body temperature and low blood circulation may result in major discomfort if not serious medical complications such as frostbite, pneumonia, or shock. Consequently, one may be discouraged from pursuing these kinds of recreational activities and may give them up altogether.

While various references uncovered in the prior art provide devices that deliver heat to a body, no device is light in weight, easily worn, and sufficiently flexible to provide free bodily movement.

U.S. Pat. No. 5,383,918 to Panetta, for example, discloses a heat conserving or cooling suit enclosure made of plastic sheet for a patient undergoing a medical procedure. The suit enclosure may effectively maintain normal body temperature during a medical procedure. However, it is not suitable for outdoor activities because the plastic sheet enclosure suit significantly limits the mobility of the user.

U.S. Pat. No. 4,572,188 to Augustine discloses an airflow cover for controlling the body temperature of a patient. The airflow cover is intended to be used during a medical treatment and faces a similar problem to that of Panetta. This invention is not suitable for outdoor use because the cover is made of a series of inflated tubes which are inflexible resulting in complete immobilization of the user.

U.S. Pat. No. 4,067,064 to Cerniway discloses a wet suit that includes conduits for delivering different portions of heated fluid to various parts of the diver's body. This invention requires the user to be attached to an external source that provides heated fluid, and therefore, greatly restricts the mobility of the user.

While these units mentioned above may be suitable for the particular purpose employed, or for general use, they would not be as suitable for the purposes of the present invention as disclosed hereafter.

SUMMARY OF THE INVENTION

It is an object of the invention to deliver heat to designated body parts.

It is another object of the invention to produce a body heating device which is simple and inexpensive in construction, and is easily worn on one's body.

It is yet another object of the invention to produce a body heating device which is light in weight and is sufficiently flexible, to provide free movement for the user.

It is a further object of the invention to produce a body heating device, where a user may selectively adjust the amount of air flowing to different body parts.

A body heating device which utilizes heat from one's own breath to warm various designated body parts during a cold outdoor activity. The device comprises a central conduit having a mouth opening, said central conduit connected to a network of tubes, and an attachment means for attaching said tubes and conduit to a person's body. The body heating device preferably includes a distribution control assembly connected between said central conduit and said network of tubes, for allowing the person to select the amount of heated air to be delivered to different body parts.

The body heating device is worn on the person's body, and each of the open ends of the tubes are placed near those areas of the body to which hot air is to be delivered. By blowing air into the mouth opening end of said central conduit, a pocket of hot air travels to the open ends of the tubes, thereby delivering hot air to the selected body parts.

To the accomplishment of the above, and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a front elevational view of the instant invention.

FIG. 2 is a cross-sectional view of the distribution control assembly.

FIG. 3 is a cross-sectional view of the distribution control assembly of the preferred embodiment.

FIG. 4 is a front elevational view of an alternative embodiment of the instant invention.

DETAILED DESCRIPTION OF THE PREFERRED EMBODIMENTS

FIG. 1 illustrates a body heating device 10 comprising a union suit 12, also known as a jump suit. The union suit 12 has arms 14, a body section 16, a neck opening 18, and a pair of legs 20. The union suit 12 has been provided with buttons 22 which open and close to allow one to get in and out of it.

Referring momentarily to FIGS. 2, and 3 the body heating device 10 further comprises a central conduit 24 having a proximal end 26, a distal end 28, and a mouth opening 30 formed at said proximal end 26. The central conduit 24 should be situated such that the mouth opening 30 is conveniently located for the user to blow into. In particular, the mouth opening should be situated at the neck opening 18.

FIG. 2 and FIG. 3 show a distribution control assembly 32 having four air flow adjustment valves 34. Each adjustment valve 34 individually allows the user to select an amount of heated air to be delivered to different body parts. Each of the air flow adjustment valves has an inlet port 36 and a pair of outlet ports 38. The inlet ports 36 of the adjustment valves 34 are connected to the central conduit 24 to allow flow of air from the central conduit 24 to the pair of outlet ports 38. A user may selectively control the volume of air flow by adjusting a knob 40 attached to each of the adjustment valves 34.

The body heating device 10 may have any number of tubes which can be placed in any manner so as to provide heated air to any location of the body. In FIG. 1 the body heating device 10 is illustrated as having a network of eight tubes 42—two hand tubes 44, two foot tubes 46, two kidney tubes 48, and two back of neck tubes 50—each tube having a connection end 52 and an open end 54. The connection ends 52 of the tubes 42 are releasably connected to the outlet ports 38. The network of tubes 42 is stitched or adhered to the inside 56 of the union suit 12 and should be sufficiently flexible to provide free movement for the user. The hand tubes 44 and the foot tubes 46 should be long enough to reach the back side of each hand and the arch of the foot, respectively.

To use the instant invention, the user wears the union suit 12 and places the open ends 54 of the tubes 42 on the desired body parts, thereby allowing heat to travel to those selected areas of the body. It is recommended that the hand tubes 44 are placed on the back side of each hand and the foot tubes 46 are placed on the arch of the foot. A user may select the amount of heat flowing to different body parts by adjusting the knobs 40 on the distribution control assembly 32. By blowing air into the mouth opening 30 of the central conduit 24, a pocket of hot air travels to the open ends 54 of the tubes 42 delivering heat to the selected body parts.

As shown in FIG. 3, in a preferred embodiment, the distribution control assembly 32 further comprises a V-valve 58 and a bleed valve 60. The V-valve 58 is attached to the inside of the central conduit 24 just above the distribution control assembly 32. The V-valve 58 prevents cold outside air from flowing into the body of the user, and at the same time, prevents the warm air inside the network of tubes 42 from escaping. The bleed valve 60 is attached to the distal end 28 of the central conduit 24 for releasing any moisture that may be trapped inside the central conduit 24.

FIG. 4 illustrates an alternative embodiment of the body heating device 10 utilizing a safety harness 62 for conveniently attaching the distribution control assembly 32, and the central conduit 24 on a person's body. In this embodiment, straps are used to secure the network of tubes 42 to a person's body. Eight straps are used in the embodiment shown in FIG. 4—two straps above the ankles 64, two straps above the knees 66, two straps above the elbow 68, and two straps above the wrist 70.

While above description contains many specificities, these should not be construed as a limitation on the scope of the invention, but rather as examples of preferred embodiments. Many other variations are possible. For example, the body heating device may also utilize a vest and straps to secure the network of tubes, the central conduit, and distribution control assembly on a person's body.

What is claimed is:

1. A body heating device for warming designated body parts utilizing body heated breath as a heating medium, comprising:

a) a central conduit having a proximal end, a distal end, and a mouth opening formed at said proximal end;

b) a network of tubes comprising one or more tubes, each of said tubes having a connection end and an open end, said connection ends of the tubes connected to said central conduit;

c) an attachment means for attaching said network of tubes and said central conduit to a person's body and situating the mouth opening near the mouth of a person using the device; and d) a distribution control assembly for receiving heated air from the central conduit and selectively distributing the heated air to each of the tubes, said assembly comprising one or more air flow adjustment valves, each of said air flow adjustment valves having an inlet port and a pair of outlet ports, the inlet ports of the adjustment valves connected to the central conduit and the connection ends of the tubes releasably connected to said outlet ports, the assembly further comprising a knob attached to each of said air flow adjustment valves.

2. The body heating device of claim 1, further comprising: a V-valve attached to the inside of the central conduit above the distribution control assembly for preventing the escape of warm air inside the network of tubes.

3. The body heating device of claim 2, further comprising: a bleed valve attached to the distal end of the central conduit for releasing any moisture trapped inside the central conduit.

\* \* \* \* \*